(12) United States Patent
Eberwine

(10) Patent No.: US 7,122,313 B2
(45) Date of Patent: Oct. 17, 2006

(54) METHODS AND KITS FOR IDENTIFYING AND QUANTIFYING RNAS AND DNAS ASSOCIATED WITH RNA AND DNA BINDING PROTEINS

(75) Inventor: James H. Eberwine, Philadelphia, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 388 days.

(21) Appl. No.: 10/344,467

(22) PCT Filed: Aug. 17, 2001

(86) PCT No.: PCT/US01/25804

§ 371 (c)(1),
(2), (4) Date: Dec. 11, 2003

(87) PCT Pub. No.: WO02/14476

PCT Pub. Date: Feb. 21, 2002

(65) Prior Publication Data

US 2004/0096839 A1     May 20, 2004

(51) Int. Cl.
*C12Q 1/68* (2006.01)
*G01N 33/53* (2006.01)
*C12P 19/34* (2006.01)

(52) U.S. Cl. .......... 435/6; 435/7.1; 435/91.1; 435/91.2

(58) Field of Classification Search ............ 435/6, 435/7.1, 91.1, 91.2
See application file for complete search history.

(56) References Cited

U.S. PATENT DOCUMENTS

| 5,922,617 | A | 7/1999 | Wang et al. ............. 436/518 |
| 6,027,890 | A | 2/2000 | Ness et al. ............. 435/6 |
| 6,087,112 | A | 7/2000 | Dale ..................... 435/6 |
| 6,238,867 | B1 * | 5/2001 | Roninson et al. ....... 435/6 |
| 6,635,422 | B1 * | 10/2003 | Keene et al. ........... 435/6 |

* cited by examiner

*Primary Examiner*—Kenneth R. Horlick
(74) *Attorney, Agent, or Firm*—Licata & Tyrrell P.C.

(57) ABSTRACT

Methods and kits for identifying RNAs and DNAs associated with an RNA or DNA binding protein via a detector specific for the binding protein or protein bound thereto which is linked to an oligonucleotide capable of directing the synthesis of cDNA copies of RNA or DNA that are in close proximity to or in the vicinity of the bound detector are provided.

7 Claims, 1 Drawing Sheet

METHODS AND KITS FOR IDENTIFYING AND QUANTIFYING RNAS AND DNAS ASSOCIATED WITH RNA AND DNA BINDING PROTEINS

FIELD OF THE INVENTION

A new methodology has now been developed for the identification and/or quantification of RNAs which associate with RNA binding proteins and DNAs which associate with DNA binding proteins. This methodology utilizes detectors specific to selected RNA or DNA binding proteins or proteins bound to these the RNA or DNA binding proteins to direct the synthesis of cDNA copies of RNAs or DNAs that are in close proximity to or in the vicinity of the detector via a selected oligonucleotide linked to the detector. Examples of detectors specific to selected RNA or DNA binding proteins include, but are not limited to, antibodies, single chain FVs (ScFVs), complementarity determining regions (CDRs) and other molecules that can interact with RNA or DNA binding proteins. Identification of RNAs associated with RNA binding proteins or DNAs associated with DNA binding proteins is useful in identifying and designing therapeutic agents which alternatively regulate the function of RNAs associated with dysfunctional RNA binding proteins or DNAs associated with dysfunctional DNA binding proteins, thereby alleviating symptoms of disease caused by the dysfunctional RNA or DNA binding proteins. This method is also useful in identifying cis-acting elements in the RNA or DNA responsible for binding to the RNA or DNA binding protein. Kits for identification and/or quantification of RNAs which associate with RNA binding proteins or DNAs which associate with DNA binding proteins are also provided.

BACKGROUND OF THE INVENTION

Cellular functioning requires the translation of mRNA into protein. Part of this process is the movement and processing of RNA from the nucleus to the cytoplasm. mRNAs in the cytoplasm are also transported to different regions within a cell where they are locally translated. Translation also occurs on ribosomes which are complexes of RNAs and proteins. The RNAs that are associated with ribosomes, as well as the mRNAs that are transported and translated, associate with proteins that facilitate the directed movement of RNAs to their proper functional place within cells. These RNA binding proteins, in association with other proteins and the cytoskeleton of the cell, are primary regulators of this movement.

RNA-binding proteins are crucial cellular integrators that are at the nexus of genetic and environmental interactions. RNA-binding proteins are responsible for the conversion of genetic DNA information into RNA (transcription), the maturation of the transcribed RNA (splicing and editing), the transport of RNA from the nucleus to the cytoplasm and transport of mRNA throughout the cytoplasm to ribosomal sites of translation. Indeed, RNA-binding proteins are responsible for regulation of the translation of RNAs. This regulation is referred to as translational control and is key in cellular regulation. Furthermore, all cellular RNAs bind to multiple RNA-binding proteins and each type of RNA-binding protein can bind to multiple mRNA species. Indeed, RNAs should be classified as functional groups not based upon the proteins that they encode (e.g. g-protein coupled receptor family) but rather by the RNA-binding proteins that they interact with since these proteins regulate the expression of the bound RNAs.

There are over 500 different RNA binding proteins within cells which are involved in modulation of various physiological functions. Characterization of RNA binding proteins has been difficult. Typically, RNA fragments are used to select RNA binding proteins from a protein lysate. Identification of RNAs associated with the RNA binding protein is also important to understand the function of the RNA binding protein and what RNAs may be affected by dysfunction of the RNA binding protein.

Determination of RNAs which bind to the RNA binding protein is usually done by screening a pool of mRNAs or mRNA fragments with an RNA binding protein to identify those RNAs which associate with the RNA binding protein. Once one RNA has been identified which associates with the RNA binding protein, nucleotide sequence similarity or predicted RNA structure is often utilized to predict what other RNAs might share these structural features and associate with the RNA binding protein. Typically, these studies utilize gel shift assays and ultraviolet light induced protein-RNA cross-linking assays. However, these assays suffer from a lack of sensitivity and specificity that often result in erroneous results.

SUMMARY OF THE INVENTION

An object of the present invention is to provide methods for identifying and/or quantifying RNAs or DNAs associated with a RNA binding protein or a DNA binding protein, respectively. In this method, a detector specific for the RNA or DNA binding protein or a protein bound to the RNA or DNA binding protein is added to cells so that the detector binds to the RNA or DNA binding protein or the protein bound thereto. Examples of detectors useful in the present invention include, but are not limited to, antibodies, single chain FVs (ScFVs), complementarity determining regions (CDRs) and other molecules that can interact with RNA or DNA binding proteins. The detector is linked to an oligonucleotide capable of directing the synthesis of cDNA copies of RNA or DNA that are in close proximity to or in the vicinity of the bound detector. cDNA copies of RNAs or DNAs in close proximity to or in the vicinity of the bound detector are then synthesized. The synthesized cDNA or aRNA amplified therefrom are then used as probes for sets of RNAs or DNAs to identify and/or quantify RNAs or DNAs by hybridization. Examples of sets of RNAs or DNAs which can be screened with these probes include, but are not limited to, DNA or RNA microarrays, RNA or DNA macroarrays, cDNA libraries, differential display libraries or other clone or oligonucleotide sets. RNAs or DNAs that hybridize to the probes and which are in close proximity to or in the vicinity of the RNA or DNA binding protein, respectively, are expected to bind to the RNA or DNA binding protein.

These methods can be used with fixed cells or tissue samples as well as with live cells.

Another object of the present invention is to provide a method for identifying a cis-acting element in an RNA responsible for binding of the RNA to an RNA binding protein. In this method, a detector specific for the RNA binding protein or a protein bound to the RNA binding protein is added to cells so that the detector binds to the RNA binding protein or the protein bound thereto. Examples of detectors useful in the present invention include, but are not limited to, antibodies, single chain FVs (ScFVs), complementarity determining regions (CDRs) and other molecules that can interact with RNA or DNA binding proteins. The detector is linked to an oligonucleotide capable of directing the synthesis of cDNA copies of mRNA that are in close proximity to or in the vicinity of the bound detector. cDNA copies of mRNAs in close proximity to or in the vicinity of the bound detector are then synthesized and the synthesized cDNA are amplified into aRNA. A library from the aRNA is then prepared and the library is sequenced to identify the 3' end region of the cDNA that should be immediately 5' to the cis-acting binding element in the RNA.

Another object of the present invention is to provide kits for identifying and/or quantifying RNAs and DNAs associated with a selected RNA binding protein or selected DNA binding protein, as well as the cis-acting element of RNAs associated with a selected RNA or DNA binding protein. Kits of the present invention comprise a detector which specifically binds the selected RNA binding protein or protein bound thereto, wherein the detector is linked to an oligonucleotide capable of directing the synthesis of cDNA copies of RNA or DNA that are in close proximity to or in the vicinity of the bound detector.

DETAILED DESCRIPTION OF THE INVENTION

Figure 1:
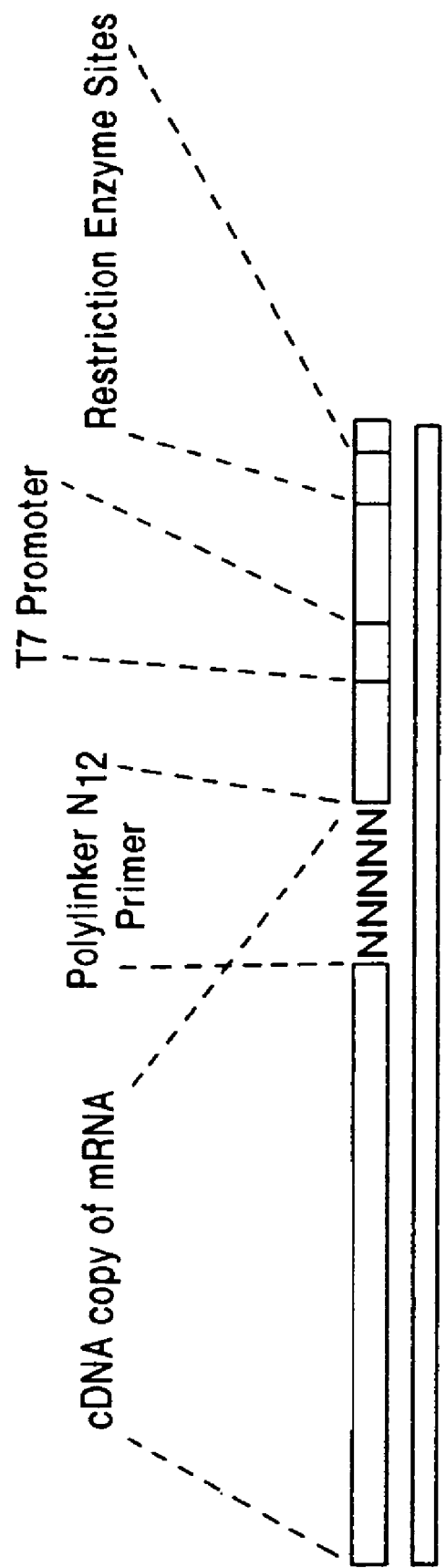
FIG. 1 provides a schematic of an oligonucleotide capable of directing the synthesis of cDNA copies of mRNA in the vicinity of a detector to which the oligonucleotide is attached.

The present invention relates to a new methodology which utilizes detectors specific to selected RNA or DNA binding proteins or selected proteins bound to a RNA or DNA binding protein to direct the synthesis of cDNA copies of RNA or DNA that are in close proximity to or in the vicinity of the bound detector. Examples of detectors specific to selected RNA or DNA binding proteins or proteins bound thereto include, but are not limited to, antibodies, single chain FVs (ScFVs), complementarity determining regions (CDRs) and other molecules that can interact with RNA or DNA binding proteins. The synthesis of cDNA copies of RNA or DNA in close proximity to or in the vicinity of detector bound to the RNA or DNA binding protein or a protein bound thereto is accomplished by attachment of a specific single stranded oligonucleotide to the detector. This oligonucleotide comprises from the 5' to the 3' end: an activatable group such as $NH_2$, $SH_2$ or O; a linker comprising approximately 6 to 18 carbons; a first nonspecific sequence of approximately 8 to 50 nucleotides; a specific restriction enzyme site of an infrequent cutter such as BamHI, EcoRI, PstI, SalI and NotI which have 4 or more bases in their restriction sites; an RNA polymerase promoter site such as T7, T3 or SP6 in sense orientation; a second stretch of nonspecific sequence approximately 10 to 70 nucleotides in length;, and a totally degenerate 8 to 20 base sequence comprising A's, G's, C's and T's in random order. A schematic of an oligonucleotide useful in the present invention is depicted in FIG. 1. The oligonucleotide is attached to the detector using well known methods such as those described in Antibodies Laboratory Manual (Harlow, E. And Lane, D. Cold Spring Harbor Labs. 1988). Attachment may be covalent or noncovalent. Examples for attaching the detector to the oligonucleotide include, but are not limited to, glutaraldehyde cross-linking and avidin-biotin interactions (wherein avidin is attached to the detector and biotin to the oligonucleotide or vice versa). In a preferred embodiment, the oligonucleotide is attached to the detector via glutaraldehyde cross linking.

Detector is then added to live cells or a fixed specimen of tissue or cells under conditions which promote specific binding of the detector to any RNA or DNA binding protein or protein bound thereto in the cells or fixed tissue or cell specimen. For fixed tissue or cell specimens the fixative is preferably paraformaldehyde or another well known fixative. This results in bringing the attached oligonucleotide to any RNAs or DNAs that are in close proximity and most preferably bound to the RNA or DNA binding protein, respectively. The detector attached oligonucleotide interacts with closely positioned RNAs or DNAs via the degenerate base sequence at the 3' end. Thus, for purposes of the present invention, by the phrase "in close proximity to" or "in the vicinity of" it is meant that the RNA or DNA is located at a position near enough to the RNA or DNA binding protein so that the oligonucleotide attached to the detector can interact with the RNA or DNA when the detector is bound to the RNA or DNA binding protein. In a preferred embodiment, the RNA or DNA is bound to the RNA or DNA binding protein, respectively. A cDNA copy of these hybridized RNAs or DNAs is then made by extension of the degenerate base 3'-end via reverse transcriptase and DNTPS present in the buffer. After cDNA synthesis, the cDNA that is attached to the detector is removed from the tissue section by NaOH treatment, the mixture is neutralized and a second strand cDNA is made by random priming in accordance with well known procedures. Once the second strand is made a functional restriction site is inserted immediately 5' to the polymerase promoter sequence. The restriction enzyme for this restriction site is then added to the DNA mixture, preferably at a concentration of 1 unit/50 µl, and the DNA is cut by the restriction enzyme to liberate the double stranded cDNA from the detector. The sample is then extracted, preferably via phenol and chloroform, and DNA is precipitated, preferably via ethanol. As will be understood by those of skill in the art upon reading this disclosure, other extraction techniques such as spin columns or separation filters and other DNA precipitation techniques such as isopropanol or evaporation can also be used.

In one embodiment, the double stranded cDNA in the precipitate is amplified using an aRNA procedure. aRNA procedures are well known and used routinely by those of skill in the art.

The cDNA, or more preferably the aRNA, can then be used as a probe to screen sets of RNA or DNA including, but not limited to, RNA or DNA microarrays, RNA or DNA macroarrays, cDNA libraries, differential display libraries and other clone or oligonucleotide sets. Resultant hybridization signals correspond to cDNA copies of RNAs or DNAs that were in close proximity to the RNA or DNA binding protein, respectively. These particular RNAs or DNAs are highly enriched for RNAs or DNAs that actually bind to the RNA or DNA binding protein, respectively.

Alternatively, the aRNA can be used to produce a library which is then sequenced to identify cis-acting elements in the RNA responsible for binding to the RNA binding protein.

Accordingly, the method of the present invention provides a means to characterize the population of RNAs and DNAs associated with selected RNA and DNA binding proteins in situ or in vivo on tissue sections. Further, the method provides a means for localizing the approximate binding site between RNA and DNA binding proteins and their cargo RNAs and DNAs, respectively.

In addition, because the amplification of RNA polymerase promoter sites such as T7 is linear, the method of the present invention can also be used to quantify RNAs and DNAs that are in close proximity, and more preferably bound, to RNA or DNA binding proteins. For example, using T7 RNA amplification, a linear amplification of the in situ transcribed mRNAs is provided and the relative abundances of the RNAs that are in close proximity, and more preferably bound, to a selected RNA binding protein can be determined.

The method of the present invention can also be used to determine the translational state of a particular mRNA or class of mRNAs. Since the abundance of each mRNA cargo that binds to or is in close proximity a particular mRNA binding protein can be quantified, detectors to the RNA-binding proteins in the ribosomal complex can be used to determine the relative abundances of mRNAs associated with the ribosome. This information is critical to understanding the translational control of gene expression. To determine the translational state of a selected RNA or set of RNAs, a first detector specific for a protein associated with a first translational complex is added to live cells or a fixed tissue or cell sample. Examples of proteins associated with the translational complex include, but are not limited to ribosomal proteins and elongation factor. The first detector is linked to an oligonucleotide which directs the synthesis of cDNA copies of mRNA that are in the vicinity of the first detector bound to the protein associated with the first translational complex. cDNA copies of mRNAs in the vicinity of the bound first detector are then synthesized and amplified into aRNA. The aRNA is used as a probe to identify RNAs by hybridization to a set of RNAs and the amount of probe hybridized, which is indicative of the relative abundance of RNAs associated with the first translational complex, is quantified. These steps are then repeated with a second detector specific for a protein associated with a second translational complex which is distinct from the first translational complex. The second detector is linked to an oligonucleotide which directs the synthesis of cDNA copies of mRNA or DNA that are in the vicinity of the second detector bound to a protein associated with the second translational complex, so that the relative abundance of RNAs associated the second translational complex can be quantified. The relative abundances of the RNAs of the first and second translational complexes are then compared so that the translational state of a selected RNA or set of RNAs can be determined.

The method of the present invention can also be used for classification of mRNAs based upon their association with particular RNA-binding proteins. For example, using the method of the present invention, mRNAs that are co-regulated by the activity of a selected RNA binding protein can be delineated by defining RNA cargos associated with a RNA binding protein. Alternatively, classification can be based upon characterization of one or more RNA binding proteins as bound to one or more mRNAs. Classification of mRNAs is important in the development of bioinformatics analyses.

Also provided in the present invention are kits for identifying RNAs and DNAs associated with selected RNA and DNA binding proteins, respectively. Kits of the present invention comprise a detector which specifically binds the selected RNA or DNA binding protein. Linked to this detector is an oligonucleotide, such as depicted in FIG. 1, which is capable of directing the synthesis of cDNA copies of RNA or DNA that are in the vicinity of the bound detector. Additional components such as the reagents used in cDNA synthesis or sets of RNAs or DNA including, but not limited to RNA or DNA microarrays, RNA or DNA macroarrays, cDNA libraries, differential display libraries and other clone or oligonucleotide sets, can also be included in these kits.

RNAs and DNAs identified via the method and kits of the present invention serve as potential therapeutic targets for intervention of the consequences of dysfunctional RNA and DNA binding proteins. Therapeutic agents which alternatively regulate the function of RNAs and DNAs identified in accordance with this method as associating with the dysfunctional RNA or DNA binding protein may be useful in alleviating symptoms of diseases, conditions or disorders resulting from the dysfunctional RNA or DNA binding protein.

For example, dysfunctional RNA binding proteins have been implicated in a number of diseases including, but not limited to, Fragile-X disease and Spinal Muscular Atrophy (SMA). Examples of DNA binding proteins include, but are certainly not limited to, DNA polymerases and transcription factors. Dysfunction of these DNA binding proteins can have dramatic implications on gene expression. The present invention provides a new means for identifying and designing therapeutic agents which alleviate symptoms of diseases, disorders and conditions such as these resulting from the dysfunctional RNA and DNA binding protein.

The methodology of the present invention was used to characterize mRNAs that associate with Translin, an RNA binding protein found in the central nervous system and various peripheral tissues. mRNAs encoding the following sequences have been identified as binding to Translin RNA binding protein via this method: ribosomal S3 protein, glutathione peroxidase, DLK, adipocyte differentiation-associated protein, phosphotyrosyl phosphatase activator, UDP-glucuronosyltransferase, U2 small nuclear protein auxiliary factor, farnesyltransferase, G/T mismatch binding protein and β-amyloid. The following ESTs were also identified as binding to this RNA binding protein: Genbank Accession No. AA0033156, AA103190, AA268309, AA165851, W20829, AA388193 and W36831.

What is claimed is:

1. A method for identifying RNAs or DNAs associated with an RNA or DNA binding protein, respectively, comprising:
    (a) adding to live cells or a fixed tissue or cell sample a detector specific for an RNA or DNA binding protein or a protein bound thereto, wherein the detector is linked to an oligonucleotide which directs the synthesis of cDNA copies of mRNA or DNA that are in the vicinity of the bound detector;
    (b) synthesizing cDNA copies of mRNAs or DNAs in the vicinity of the bound detector; and
    (c) using the cDNA or aRNA amplified therefrom as a probe to identify RNAs or DNAs by hybridization to a set of RNAs or DNAs.

2. The method of claim 1 wherein the set of RNAs or DNAs is selected from the group consisting of RNA or DNA microarrays, RNA or DNA macroarrays, cDNA libraries, differential display libraries, and other clone or oligonucleotide sets.

3. The method of claim 1 wherein the oligonucleotide attached to the detector comprises from its 5' to 3' end an activatable primary amine group on a carbon linker, a first nonspecific sequence of 8 to 50 nucleotides, a restriction enzyme site selected from the group consisting of BamHI, EcoRI, PstI, SalI and NotI, a T7 RNA polymerase promoter site in sense orientation, a second stretch of nonspecific sequence 10 to 70 nucleotides in length, and a totally degenerate sequence 8 to 20 bases in length.

4. A method for quantifying the relative abundance of RNA or DNA in close proximity or bound to a RNA or DNA binding protein, respectively, comprising:
  (a) adding to live cells or a fixed tissue or cell sample a detector specific for an RNA or DNA binding protein or a protein bound thereto, wherein the detector is linked to an oligonucleotide which directs the synthesis of cDNA copies of RNA or DNA that are in the vicinity of the bound detector, said oligonucleotide comprising a T7 RNA polymerase promoter site;
  (b) synthesizing cDNA copies of RNAs or DNAs in the vicinity of the bound detector;
  (c) using the cDNA or aRNA amplified therefrom as a probe to identify RNAs or DNAs by hybridization to a set of RNAs or DNAs; and
  (d) quantifying the amount of probe hybridized to the set of RNAs or DNAs, wherein the amount of hybridized probe is indicative of the relative abundance of RNAs or DNAs bound to the RNA or DNA binding protein.

5. A method for identifying a cis-acting element in an RNA responsible for binding of the RNA to an RNA binding protein comprising:
  (a) adding to live cells or a fixed tissue or cell sample a detector specific for an RNA binding protein or a protein bound thereto, wherein the detector is linked to an oligonucleotide which directs the synthesis of cDNA copies of mRNA or DNA that are in the vicinity of the bound detector;
  (b) synthesizing cDNA copies of mRNAs in the vicinity of the bound detector;
  (c) amplifying the cDNA into aRNA;
  (d) preparing a library from the aRNA;
  (e) sequencing the library; and
  (f) comparing sequences of the library to a full length sequence so that cis-acting elements in the RNA in the vicinity of the bound detector are identified.

6. A method for determining a translational state of a selected RNA or set of RNAs comprising:
  (a) adding to live cells or a fixed tissue or cell sample a first detector specific for a protein associated with a first translational complex, wherein the first detector is linked to an oligonucleotide which directs the synthesis of cDNA copies of mRNA that are in the vicinity of the first detector bound to the protein associated with the first translational complex;
  (b) synthesizing cDNA copies of mRNAs in the vicinity of the bound detector;
  (c) amplifying the cDNA into aRNA;
  (d) using the aRNA as a probe to identify RNAs by hybridization to a set of RNAs;
  (e) quantifying the amount of probe hybridized to the set of RNAs, wherein the amount of hybridized probe is indicative of the relative abundance of RNAs associated with the first translational complex;
  (f) repeating steps (a) through (e) with a second detector specific for a protein associated with a second translational complex, wherein the second detector is linked to an oligonucleotide which directs the synthesis of cDNA copies of mRNA or DNA that are in the vicinity of the second detector bound to the protein associated with the second translational complex, so that the relative abundance of RNAs associated the second translational complex can be quantified; and
  (g) comparing the relative abundances of the RNAs of the first and second translational complexes so that the translational state of a selected RNA or set of RNAs can be determined.

7. A kit for identifying RNAs associated with a selected RNA binding protein or DNAs associated with a selected DNA binding protein comprising a detector which specifically binds the selected RNA binding protein or DNA binding protein or proteins attached thereto, wherein the detector is linked to an oligonucleotide which directs the synthesis of cDNA copies of RNA or DNA that are in the vicinity of the bound detector.

* * * * *